US 6,648,858 B2

(12) United States Patent
Asbaghi

(10) Patent No.: US 6,648,858 B2
(45) Date of Patent: Nov. 18, 2003

(54) SAFETY DEVICE FOR A SHEATHED, PREFILLED INJECTION SYRINGE

(75) Inventor: Hooman A. Asbaghi, Del Mar, CA (US)

(73) Assignee: Visual Connections, Inc., San Diego, CA (US)

( * ) Notice: Subject to any disclaimer, the term of this patent is extended or adjusted under 35 U.S.C. 154(b) by 40 days.

(21) Appl. No.: 10/032,342

(22) Filed: Dec. 21, 2001

(65) Prior Publication Data
US 2003/0120218 A1 Jun. 26, 2003

(51) Int. Cl.⁷ ................................................ A61M 5/32
(52) U.S. Cl. ........................................................ 604/198
(58) Field of Search ......................... 604/181, 186–188, 604/192, 195, 197–198, 215, 218, 229, 239–243, 110, 115–117; 128/919

(56) References Cited

U.S. PATENT DOCUMENTS

| 5,061,251 A | * | 10/1991 | Juhasz ............................ 604/198 |
| 5,167,640 A | * | 12/1992 | Balding .......................... 604/192 |
| 5,176,656 A | * | 1/1993 | Bayless .......................... 128/919 |
| 5,242,401 A | | 9/1993 | Colsky |
| 5,242,420 A | * | 9/1993 | Martin ............................ 604/198 |
| 5,267,977 A | | 12/1993 | Feeney, Jr. |
| 5,279,566 A | * | 1/1994 | Kline et al. ..................... 604/110 |
| 5,295,975 A | | 3/1994 | Lockwood, Jr. |
| 5,376,080 A | | 12/1994 | Petrussa |
| 5,389,085 A | | 2/1995 | D'Alessio |
| 5,403,286 A | | 4/1995 | Lockwood, Jr. |
| 5,540,667 A | * | 7/1996 | Tanner, II ....................... 604/192 |
| 6,030,366 A | * | 2/2000 | Mitchell ......................... 604/192 |

* cited by examiner

Primary Examiner—LoAn H. Thanh
(74) Attorney, Agent, or Firm—Nydegger & Associates

(57) ABSTRACT

A safety device for a sheathed injection syringe includes a needle guard having a dilatable opening at its distal tip. A plurality of slits are formed in the guard extending proximally from the distal tip of the guard to create the dilatable opening. When the guard is in the relaxed state, the opening is relatively large to allow the sheath to pass through the guard during attachment of the safety device to the syringe. A ring having a lug is positioned over the guard and is moveable to contract the opening. The contracted opening allows the syringe to be used at non-normal injection angles. A cover is provided having an aperture for engagement with the needle sheath and a slot for engagement with the lug. During withdrawal of the cover, the sheath is removed from the needle and the ring is moved, contracting the guard opening.

19 Claims, 3 Drawing Sheets

SAFETY DEVICE FOR A SHEATHED, PREFILLED INJECTION SYRINGE

FIELD OF THE INVENTION

The present invention pertains generally to syringes for medical use. More particularly, the present invention pertains to safety devices for prefilled injection syringes. The present invention is particularly, but not exclusively, useful for safely removing the sheath from a syringe and thereafter providing a passive guard assembly that is configured to allow for injections at relatively large angles from the normal at the injection site.

BACKGROUND OF THE INVENTION

Recent research from the Centers for Disease Control and Prevention (CDC) shows that approximately 384,000 needlesticks or similar injuries occur among health care workers in U.S. hospitals each year. Unfortunately, each accidental needlestick has the potential to expose a health care worker to a life-threatening virus such as hepatitis or HIV. In addition to the needlesticks that occur in hospitals, accidental needlesticks can also occur in other health care settings. For example, needlestick injuries can occur at clinics or during home health care. In fact, some studies have estimated that over 600,000 needlesticks occur in the U.S. each year, and approximately 1,000 of these accidental needlesticks result in a life-threatening infection.

For each accidental needlestick, health care providers are obligated to test and counsel the exposed worker. Further, follow-up testing for HIV must be conducted approximately six months after the exposure. It is to be appreciated that the costs associated with the testing, lab work, the workers lost time, and the associated tracking and administrative costs, can be considerable.

Accidental needlesticks can occur in several ways. For example, a sudden movement by the patient can cause a health care worker to lose control of a syringe, resulting in injury. Attempts to manually recap a needle after filling the syringe with a medicament or attempts to recap a syringe following an injection can also result in injury. Moreover, injuries often result when contaminated, unprotected needles are left unattended or disposed of improperly. In addition to accidental needlesticks, unnecessary exposure to blood-borne pathogens can result when a health care worker mistakenly reuses a contaminated needle on a patient.

Prefilled injection syringes (i.e. syringes that are delivered to the health care worker containing a single dose of medicament) are commonly used for vaccines, low molecular weight heparins and many new biotechnology drugs. By using a prefilled injection syringe, several needle handling steps are eliminated for the health care worker, and the risk of inadvertent re-use is lowered. Even with these advantages, the risk of exposure to a used needle is still presented by prefilled injection syringes. As such, a safety device that passively covers and protects the needle of a prefilled injection syringe after an injection is desirable. More specifically, a safety device that can be easily installed is needed to allow the large amount of existing prefilled syringes to be used safely.

Heretofore, prefilled syringes have generally been delivered to the user with a sheath installed over the needle to protect the needle during transportation and handling. Some currently available safety devices require the user to remove the sheath manually before installing a passive safety guard. A safer alternative is to provide a passive safety guard that can be installed before removal of the sheath. For this type of installation, the passive guard system is generally sized to fit over the sheath. Unfortunately, passive guard devices having a large diameter distal tip (i.e. large enough to fit over the needle sheath) often jam during an injection, especially when the syringe is used to perform an injection at a non-normal angle to the injection surface.

In light of the above, it is an object of the present invention to provide a passive guard system for installation over a sheathed, prefilled injection syringe that safely removes the sheath and subsequently allows for injections at relatively large angles from the normal at the injection site. It is another object of the present invention to provide a safety device for a sheathed prefilled injection syringe which allows the safety device to be installed on the syringe while the needle remains sheathed yet does not jam during injections at large angles from the normal at the injection site. It is yet another object of the present invention to provide a safety device that is installable on a sheathed prefilled injection syringe that passively covers the needle after an injection, locking a portion of the guard assembly over the tip of the needle to prevent accidental needlesticks or inadvertent reuse of the syringe. Yet another object of the present invention is to provide a safety device for a sheathed prefilled injection syringe that is easy to use, relatively simple to implement, and comparatively cost effective.

SUMMARY OF THE PREFERRED EMBODIMENTS

The present invention is directed to a safety device for use in conjunction with a sheathed, prefilled injection syringe during an injection. In operational overview, the safety device is first installed onto the sheathed, prefilled injection syringe. With the safety device installed on the syringe, a portion of the safety device (a cover) is removed. The removal of the cover performs two separate functions. First, removal of the cover removes the sheath from the syringe, exposing the syringe needle. Second, as detailed further below, removal of the cover reconfigures a passive guard assembly in the safety device into a configuration that is suitable for an injection. During an injection, a portion of the passive guard assembly is allowed to translate relative to the injection needle. This relative movement allows for needle penetration into the patient to the proper depth during an injection. Upon withdrawal of the needle from the patient, this relative movement allows the guard assembly to passively re-cover the needle, locking a portion of the guard assembly over the tip of the needle to prevent accidental needlesticks or inadvertent reuse of the syringe.

In greater structural detail, the passive guard assembly of the safety device includes a guard, a housing and a coil spring. For the present invention, a portion of the housing is preferably formed as an elongated, hollow cylinder that is large enough to slide over the syringe barrel of the prefilled injection syringe allowing attachment of the proximal end of the housing to the finger guard of the syringe. Like the housing, the guard is preferably formed as an elongated, hollow cylinder and defines a longitudinal axis. The proximal end of the cylindrical guard is sized for insertion into the distal end of the housing. With this combination of structure, the housing is disposed over the guard allowing both axial and rotational movement between the guard and housing. Additionally, a biasing mechanism, such as a spring, is mounted between the guard and the housing to urge the guard in a distal direction, relative to the housing. A plug formed on the guard interacts with a channel formed in the housing to control relative movement between the guard and the housing during an injection.

Importantly for the present invention, the guard extends to a distal tip that is formed with a dilatable opening. Functionally, the distal portion of the guard is reconfigurable between a first configuration in which the opening is relatively large and a second configuration in which the opening is relatively small. With the distal portion of the guard in the first configuration, the relatively large opening allows the sheathed needle of the injection syringe to pass through the end of the guard during attachment of the safety device to the syringe. On the other hand, in the second configuration, the relatively small opening allows for syringe injections at relatively large angles from the normal at the injection site.

Structurally, to create the dilatable opening, the distal portion of the guard is formed having a shape that is similar to the shape of a collet. Specifically, a plurality of slits are formed in the distal portion of the guard extending proximally from the distal tip of the guard. When the distal portion of the guard is in the relaxed state (i.e. no external forces are acting on the distal portion of the guard), the distal portion of the guard is in the first configuration, and accordingly, the opening is relatively large. To reconfigure the guard and contract the opening, the safety device further includes a moveable ring that is positioned over the distal portion of the guard. In greater detail, the ring is moveable from a proximal position wherein the distal portion of the guard is in a relaxed state and the opening is relatively large, to a distal position wherein the distal portion of the guard is radially contracted and the opening is relatively small.

To facilitate movement of the ring over the guard, the ring is formed with a lug that extends from the ring. For the present invention, the safety device further includes a cover for interaction with the lug. More specifically, one function of the cover is to engage the lug and thereby move the lug and ring distally as the cover is withdrawn from the injection syringe. In greater detail, the cover is preferably shaped as an elongated hollow cylinder having an open proximal end. An axially aligned slot is formed in the cylindrical wall of the cover for cooperative interaction with the lug on the moveable ring. To allow the lug to be located in the slot of the cover during assembly of the safety device, axially aligned slits are formed in the proximal end of the cover. These slits extend distally from the proximal end of the cover, and provide the proximal end of the cover with enough radial flexibility to allow the cover to fit over the ring and lug when the cover is assembled onto the guard. With the lug positioned in the slot of the cover, removal of the cover causes the lug and ring to move distally, reconfiguring the distal portion of the guard.

In accordance with the present invention, the distal end of the cylindrical cover is closed by a substantially flat closing wall. Importantly, an aperture is formed in the closing wall for receiving and holding the sheath of the prefilled injection syringe. For the present invention, the aperture is defined by a surrounding edge that is distally tapered. This taper allows the resilient sheath to pass into the aperture and become affixed to the cover when the safety device is installed onto the sheathed, prefilled injection syringe. With the sheath attached to the cover, the sheath can be safely removed from the prefilled injection syringe when the cover is withdrawn from the guard assembly.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
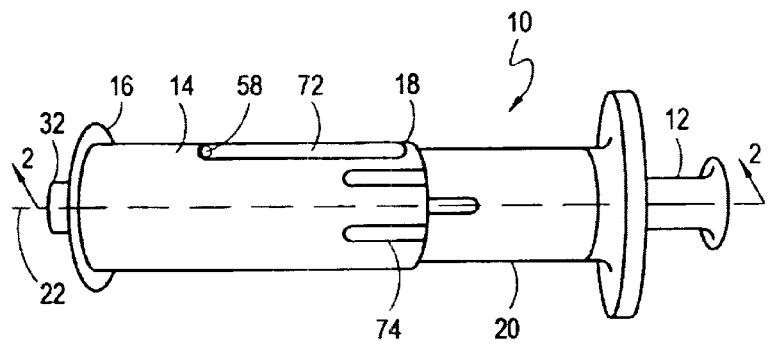
FIG. 1 is a perspective view of a safety device in accordance with the present invention installed on a prefilled injection syringe.

Referring initially to FIG. 1, a safety device 10 in accordance with the present invention is shown installed on a sheathed prefilled injection syringe 12. As shown, the device 10 includes a cover 14 that is preferably cylindrically shaped and has a distal end 16 and a proximal end 18. As further shown, the device 10 includes a housing 20 that is also substantially cylindrically shaped. When assembled and installed on the syringe 12, the cover 14 and housing 20 of the device 10 are both centered along an axis 22, as shown in FIG. 1.

Figure 2:
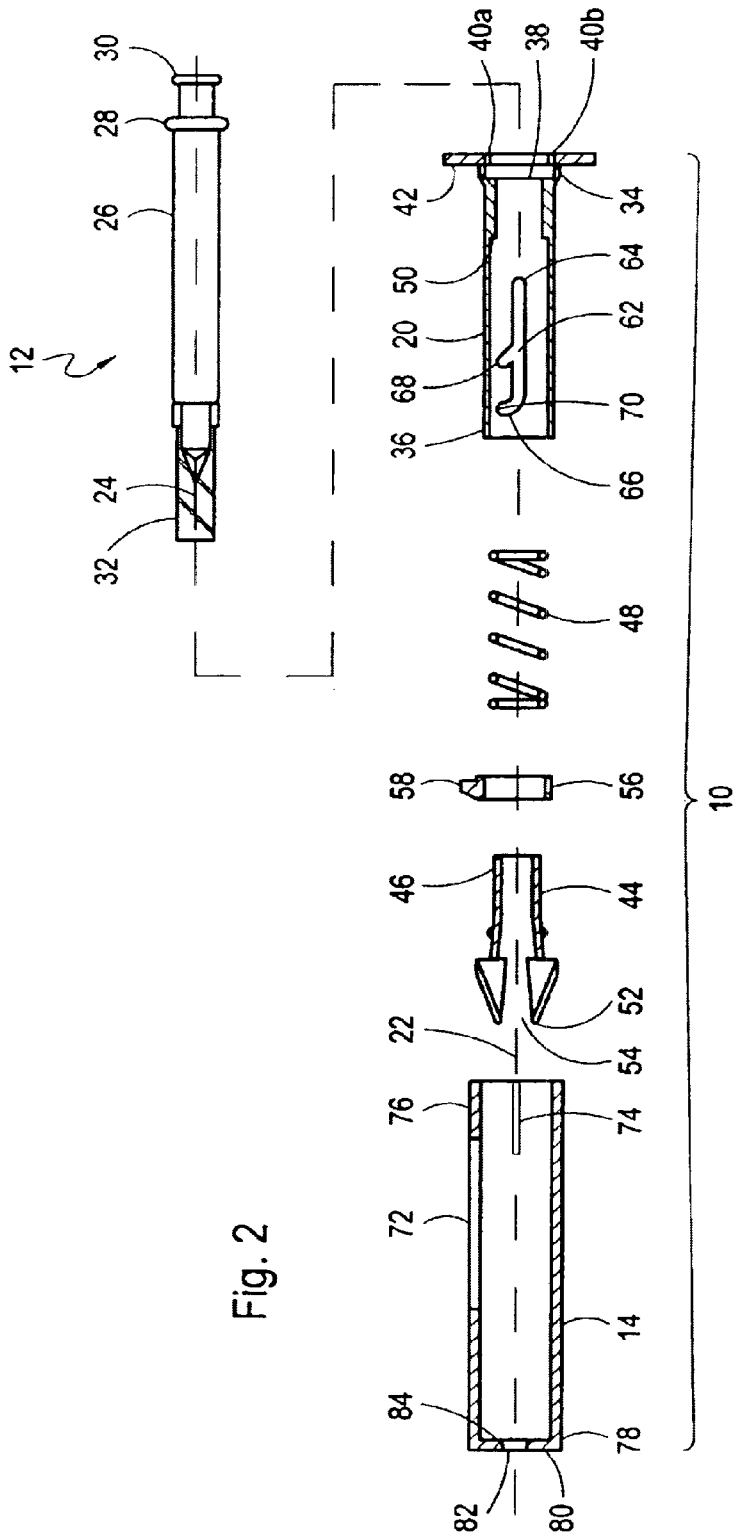
FIG. 2 is an exploded sectional view of a safety device in accordance with the present invention together with a prefilled injection syringe as seen along line 2—2 in FIG. 1.

Referring now to FIG. 2, an exemplary, sheathed, prefilled injection syringe 12 for use with the present invention is shown together with the safety device 10. As shown, the prefilled syringe 12 includes a hollow needle 24 mounted on a syringe barrel 26. A finger flange 28 is formed at the proximal end of the syringe 12 to aid in depressing the plunger 30 of the syringe 12. Further, it is to be appreciated that the prefilled syringe 12 includes a single dose of medicament that is generally placed in the syringe 12 prior to delivering the syringe 12 to the point of use. Further, needle 24 of the prefilled syringe 12 is generally covered with a sheath 32 immediately after the filling of the syringe 12 with medicament to protect the needle 24 during handling prior to use.

Referring still to FIG. 2, it can be seen that the cylindrical housing 20 is hollow and is open at both its proximal end 34 and its distal end 36. For the present invention, as shown, the housing 20 is sized large enough to be slid over the sheath 32 and syringe barrel 26 of the prefilled syringe 12. As further shown, a flat 38 is formed at the proximal end 34 of the housing 20 to allow the finger flange 28 of the prefilled syringe 12 to seat against the housing 20. Clips 40a, b extend from the housing 20 to hold and lock the housing 20 against the finger flange 28 of the prefilled syringe 12 when the device 10 is installed on the prefilled syringe 12. As shown, a beveled surface on each clip 40a, b allows the finger flange 28 of the syringe 12 to pass the clips 40a, b and lock against the flat 38. As further shown, a replacement finger flange 42 is formed at the proximal end 34 of the housing 20 to aid in depressing the plunger 30 during an injection.

With continued reference to FIG. 2, it can be seen that the device 10 further includes a guard 44 that is formed as a hollow cylinder. When assembled in the device 10, the guard 44 is substantially centered on the axis 22. As further shown in FIG. 2, the guard 44 has a proximal end 46 that is sized to allow the proximal end 46 of the guard 44 to be inserted into the distal end 36 of the housing 20. With this combination of structure, the housing 20 can be disposed over the proximal end 46 of the guard 44 to thereby allow both axial and rotational movement between the guard 44 and housing 20. The device 10 further includes a coil spring 48 to urge the guard 44 in a distal direction, relative to the housing 20. As shown, the spring 48 is sized to allow for insertion of the spring 48 into the distal end 36 of the housing 20. A ledge 50 is formed in the housing 20 to seat the proximal end of the spring 48. It is to be appreciated from FIG. 2 that the distal end of the spring 48 seats against the edge of the guard 44 at the proximal end 46 of the guard 44.

Figure 3A:
FIG. 3A is a sectional view of a guard shown in the contracted state.

As best appreciated with cross reference to FIGS. 2 and 3A, it can be seen that the guard 44 extends to a distal tip 52 that is formed with a dilatable opening 54. Functionally, the distal portion of the guard 44 is reconfigurable between a first configuration (shown in FIG. 2) in which the opening 54 is relatively large and a second configuration (shown in FIG. 3A) in which the opening 54 is relatively small. With the distal portion of the guard 44 in the first configuration, the relatively large opening 54 allows the sheath 32 of the injection syringe 12 to pass through the distal tip 52 of the guard 44 during attachment of the safety device 10 to the syringe 12. On the other hand, in the second configuration, the relatively small opening 54 allows for syringe injections at relatively large angles from the normal at the injection site.

Figure 4A:
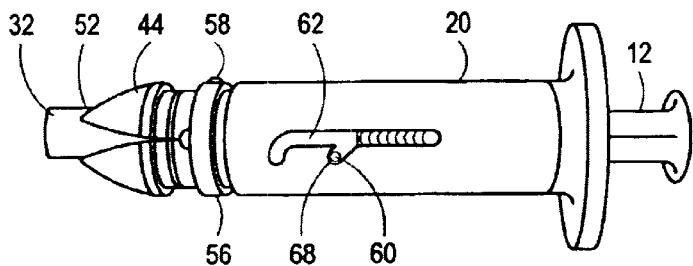
FIG. 4A is a perspective view of a safety device in accordance with the present invention after installation onto a sheathed prefilled injection syringe (for clarity, the cover of the safety device is not shown)

As shown in FIGS. 2, 3A and 4A, the distal portion of the guard 44 is formed having a shape that is similar to the shape of a collet to create the dilatable opening 54. Specifically, as shown, a plurality of slits are formed in the distal portion of the guard 44 extending proximally from the distal tip 52 of the guard 44. When no external forces are acting on the distal portion of the guard 44, (i.e. the distal portion of the guard 44 is in the relaxed state), the opening 54 is relatively large, as shown in FIGS. 2 and 4A.

As shown in FIG. 2, the safety device 10 further includes a moveable ring 56 that is positionable over the distal portion of the guard 44 to reconfigure the guard 44 and contract the opening 54. As further shown, the ring 56 is formed with a lug 58 that extends outwardly from the axis 22. It is to be appreciated that the ring 56 is moveable over the guard 44 and along the axis 22. Specifically, the guard 44 is moveable from a proximal position wherein the distal portion of the guard 44 is in a relaxed state and the opening 54 is relatively large (relaxed guard shown in FIG. 2), to a distal position wherein the distal portion of the guard 44 is radially contracted and opening 54 is relatively small (guard 44 shown contracted in FIGS. 3A and 3B).

Figure 3B:
FIG. 3B is a sectional view of a guard as in FIG. 3A but rotated 90 degrees about the axis of the guard to show the plug of the guard.

Referring now with cross reference to FIGS. 2, 3B and 4A, it can be seen that the guard 44 is formed with plug 60 that extends outwardly from the axis 22. Further, the housing 20 is formed with channel 62 that extends through the cylindrical wall of the housing 20. As shown, the guard 44 can be disposed within the housing 20, with the plug 60 inserted into the channel 62. Specifically, the proximal end 46 of the guard 44 can be deformed slightly and then pressed into the distal end 36 of the housing 20. Also shown, the linear channel 62 is aligned substantially parallel to the longitudinal axis 22 and is formed with a proximal end 64 and a distal end 66. Further, the channel 62 is formed with a latching cutout 68 positioned between the proximal end 64 and the distal end 66, and a locking cutout 70 positioned at the distal end 66.

As best seen in FIG. 2, the cylindrical cover 14 is hollow and formed with an open proximal end. When assembled in the device 10, the cover 14 is centered substantially on the axis 22. As shown, an axially aligned slot 72 is formed in the cylindrical wall of the cover 14 for cooperative interaction with the lug 58 on the moveable ring 56. Axially aligned slits 74 are formed in the proximal end 76 of the cover 14 to allow the lug 58 to be located in the slot 72 of the cover 14 during assembly of the safety device 10. As shown in FIG. 2, slits 74 extend distally from the proximal end 76 of the cover 14, and provide the proximal end 76 of the cover 14 with enough radial flexibility to allow the cover 14 to fit over the ring 56 and lug 58 when the cover 14 is assembled onto the guard 44.

With continued reference to FIG. 2, it can be seen that the distal end 78 of the cylindrical cover 14 is closed by a substantially flat closing wall 80. Importantly, an aperture 82 is formed in the closing wall 80 for receiving and holding the sheath 32 of the prefilled injection syringe 12. For the present invention, the aperture 82 is defined by a surrounding edge 84 that is distally tapered. This taper allows the sheath 32 to pass into the aperture 82 and become affixed to the cover 14 when the safety device 10 is installed onto the sheathed, prefilled injection syringe 12.

To use the device 10, the device 10 is first assembled and the assembled device 10 is installed on a sheathed, prefilled injection syringe 12. The assembly of the device 10 can best be appreciated with reference to FIG. 2. To assemble the device 10, the ring 56 is first slid over the proximal end 46 of the guard 44, leaving the distal portion of the guard 44 relaxed, and consequently, with a large opening 54 at the distal tip 52 of the guard 44. Next, the proximal end 46 of the guard 44 and the spring 48 are inserted into the distal end 36 of the housing 20 and the plug 60 of the guard 44 is located in the latching cutout 68 of the channel 62. Next, the proximal end 76 of the cover 14 is inserted over the distal tip 52 of the guard 44 and the ring 56 until the lug 58 is located in the slot 72 of the cover 14. At this point, the assembled device 10 can be installed on a sheathed, prefilled injection syringe 12.

The installation of the assembled device 10 onto a sheathed, prefilled injection syringe 12 can best be appreciated with cross-reference to FIGS. 1, 2 and 4A. To install the device 10, the sheathed end of the injection syringe 12 is inserted through the housing 20, spring 48, ring 56, guard 44 and cover 14 until the sheath 32 passes through the aperture 82 of the cover 14. When the device 10 is properly installed on the syringe 12, the finger flange 28 of the prefilled syringe 12 seats against the flat 38 formed at the proximal end 34 of the housing 20, and the clips 40a, b hold and lock the housing 20 against the finger flange 28 of the prefilled syringe 12. FIG. 1 shows the device 10 after installation on the sheathed prefilled injection syringe 12. FIG. 4A also shows the device 10 after installation on the sheathed prefilled injection syringe 12, but in FIG. 4A, the cover 14 is not shown to allow the relationship between the ring 56, guard 44 and sheath 32 after installation of the device 10. As shown in FIG. 4A, after installation of the device 10, the ring 56 is positioned proximal to the distal portion of the guard 44, and consequently, the opening 54 (shown in FIG. 2) is large to allow the sheath 32 to extend through the distal tip 52 of the guard 44. FIG. 4A also shows that after installation, the plug 60 is located in the channel 62 at the latching cutout 68.

Figure 4B:
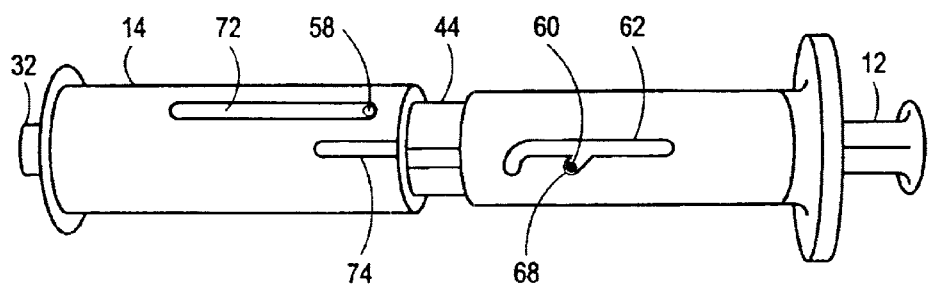
FIG. 4B is a perspective view of a protective device as shown in FIG. 1 during removal of the cover.

With the device 10 assembled and installed on the syringe 12, an injection can be performed. With cross reference to FIGS. 1, 4B and 4C, it can be seen that to perform an injection, the cover 14 is first withdrawn distally from the syringe 12 and the remainder of the device 10. The initial, distal movement of the cover 14 pulls the sheath 32 distally. During this time, the lug 58 travels within the slot 72 until the lug 58 reaches the proximal end of the slot 72. The slot 72 is configured to ensure that the sheath 32 clears the guard 44 before the lug 58 reaches the proximal end of the slot 72. After the lug 58 reaches the proximal end of the slot 72, further distal movement of the cover 14 pulls the lug 58 and ring 56 distally over the guard 44 reconfiguring the distal portion of the guard 44 and contracting the opening 54 (shown in FIG. 2) at the distal tip 52 of the guard 44. A rim 86 formed in the guard 44 is provided to maintain the ring 56 in the distal position wherein the opening 54 is contracted.

Figure 4C:
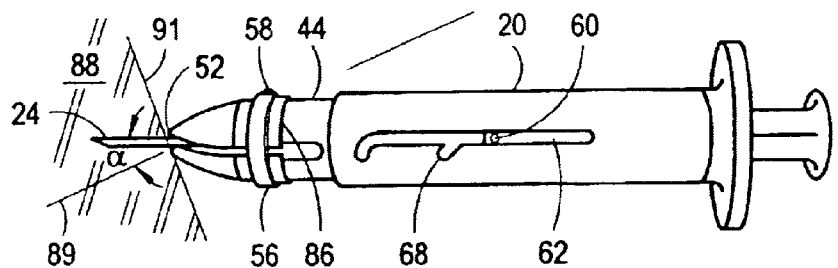
FIG. 4C is a perspective view of the safety device and syringe as shown in FIG. 1 after the cover and sheath have been withdrawn and after the distal portion of the guard has been reconfigured and the needle of the syringe has been inserted into the body of a patient.

Next, as shown in FIG. 4C, the needle 24 is inserted into the body of the patient 88 until the guard 44 contacts the patient 88. The syringe 12 and housing 20 can be further translated towards the patient 88, inserting the needle 24 to the proper penetration depth. Thus, the housing 20 moves relative to the guard 44 during insertion of the needle 24 into the patient 88. By cross referencing FIGS. 4B and 4C it can be seen that during the penetration of the patient 88 with the needle 24, the plug 60 is directed from the latching cutout 68, into the track of the channel 62 and towards the proximal end of the channel 62. Once the needle 24 is inserted into the patient 88 at the proper depth, fluid medicament can be injected into the patient 88 by depressing the plunger 30 of the syringe 12. As shown in FIG. 4C, one of the advantages of the present invention is that injections can be made at relatively large angles, α, from the normal 89 of the injection surface 91. In particular, the reconfigured distal tip 52 of the guard 44 and the associated contracted opening 54 (shown in FIG. 2) allow for injections at large angles, α, relative to the injection surface.

Figure 4D:
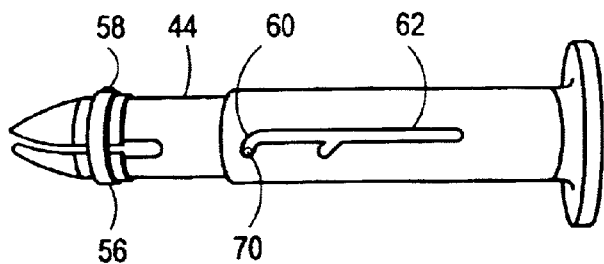
FIG. 4D is a perspective view of a safety device and syringe as shown in FIG. 4C after the needle of the prefilled syringe has been withdrawn from the body of a patient.

With cross reference now to FIGS. 4C and 4D, it can be seen that during the withdrawal of the needle 24 from the patient 88, the needle 24, housing 20 and syringe 12 move in a proximal direction relative to the guard 44. Specifically, the spring 48 (shown in FIG. 2) expands to hold the guard 44 against the patient 88 while the needle 24 is withdrawn. During the withdrawal of the needle 24 from the patient 88, the spring 48 (shown in FIG. 2) expands to translate the plug 60 along the channel 62 towards the distal end of the channel 62.

After the needle 24 is completely withdrawn from the patient 88, the syringe 12 and the needle 24 are pulled away from the body of the patient 88. During this movement, the spring 48 (shown in FIG. 2) continues to expand causing the guard 44 and plug 60 to move distally until the plug 60 reaches the distal end of the channel 62. At the distal end of the channel 62, a guide ramp formed in the channel 62 causes the plug 60 to move azimuthally (with respect to the axis 22) and axially into the locking cutout 70. Thus, the guard 44 rotates relative to the housing 20 as the plug 60 moves from the linear portion of the channel 62 into the locking cutout 70. Importantly, with the plug 60 located in the locking cutout 70, the guard 44 is locked over the hollow needle 24 of the syringe 12 to protect against accidental needlesticks or inadvertent reuse.

Figure 5A:
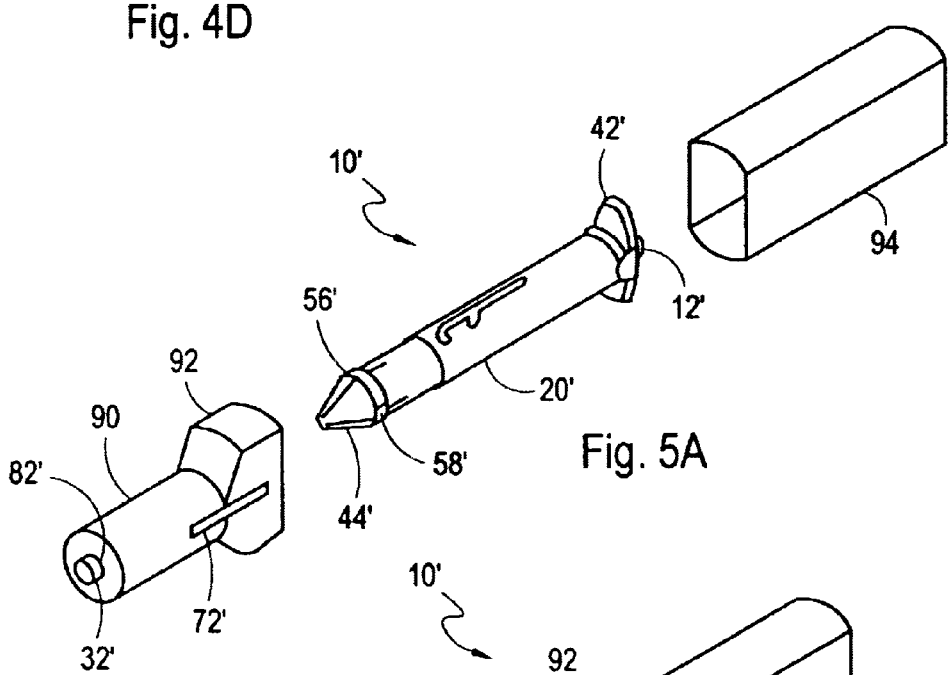
FIG. 5A is an exploded, perspective view of an alternate embodiment for the present invention wherein the safety device includes a plunger cover.
Figure 5B:
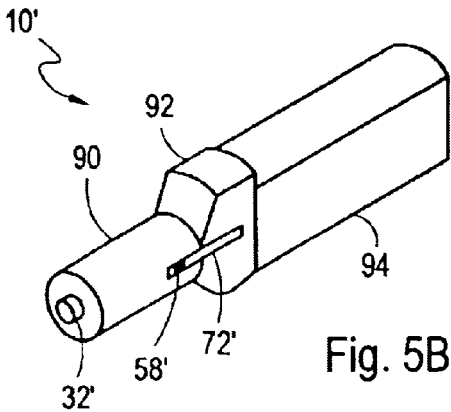
FIG. 5B is a perspective view of the alternate embodiment shown in FIG. 5A, showing the plunger cover installed on the sheathed, prefilled injection syringe.

FIGS. 5A and 5B show another embodiment of a safety device 10' in accordance with the present invention. For clarity, the prime (') has been used to denote elements in the embodiment shown in FIGS. 5A and 5B that are similar or identical in nature to like-numbered elements in the embodiment shown in FIG. 14. As shown in FIG. 5A, the safety device 10' includes a modified cover 90 that is formed with a flange 92 at the distal end. Like the cover 14 shown in FIGS. 1–4, the modified cover 90 is formed with an aperture 82' for engaging and removing the sheath 32'. Also like the cover 14 shown in FIGS. 1–4, the modified cover 90 is formed with slot 72' for interaction with the guard 44', ring 56' and lug 58' of the safety device 10'. In this embodiment, the safety device 10' also includes a plunger cover 94 for engagement with the flange 92 of the modified cover 90. With cross reference to FIGS. 5A and 5B, it is to be appreciated that the plunger cover 94 can be engaged with the modified cover 90 to protect the plunger 12 from being damaged or inadvertently depressed during handling of the assembled safety device 10'. Flats formed in the plunger cover 94 and flange 92 prevent the assembled safety device 10' from unwanted rolling during storage and handling.

While the particular safety device for a sheathed prefilled injection syringe as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A safety device for use with a sheathed, prefilled injection syringe, said safety device comprising:

a needle guard having an end and formed with a dilatable opening at said end, said end being reconfigurable between a first configuration wherein said opening is relatively large and a second configuration wherein said opening is relatively small, said relatively large opening for allowing the sheath of the injection syringe to pass through said end of said needle guard during attachment of said needle guard to the syringe, and said relatively small opening for covering and protecting the needle of the syringe after an injection; and a means for reconfiguring said end of said needle guard from said first configuration to said second configuration after removal of the sheath from the injection syringe; and a means for removing said sheath from said prefilled syringe and for activating said reconfiguring means.

2. A safety device as recited in claim 1 wherein said reconfiguring means comprises a ring, said ring being positionable over said needle guard and moveable from a first position, wherein said dilatable opening is relatively large to a second position wherein said dilatable opening is relatively small.

3. A safety device as recited in claims 2 wherein said reconfiguring means further comprises a lug that is attached to said ring.

4. A safety device as recited in claim 3 wherein said removing and activating means comprises a cover for insertion over said needle guard, said cover being formed as an elongated tube formed with a linear slot with said lug insertable into said slot, said slot having a proximal end to engage said lug and said ring during movement of said cover relative to the needle guard to move said ring from said first position to said second position.

5. A safety device as recited in claim 4 wherein said cover has an open end to allow said cover to be disposed over the needle guard and a partially closed end, said partially closed end formed with an aperture for receiving the sheath of the prefilled injection syringe and affixing the sheath to the cover to allow the sheath to be removed from the prefilled injection syringe when the cover is withdrawn from the needle guard.

6. A safety device as recited in claim 1 wherein said needle guard comprises:
   a first member having a distal end and a proximal end, said first member formed as a hollow cylinder defining an axis and formed with at least one plug extending radially outwardly therefrom;
   a second member disposed on said first member for reciprocal movement thereon, said second member having a means for affixing said second member to the injection syringe with the needle extending through said first member, said second member being formed with a linear channel aligned substantially parallel to said axis with said plug inserted into said channel for movement therein, said channel having a proximal end and a distal end with a latching cutout formed therebetween and a locking cutout formed at said distal end of said channel; and
   a biasing means disposed between said first member and said second member to urge said first member and said second member in opposite axial directions and, in sequence, to initially hold said plug in said latching cutout to partially extend said needle from said first member, to then allow said plug to move in said channel toward said proximal end of said channel to further extend said needle from said first member in response to an external force against said first member, and to subsequently move said plug into said locking cutout at said distal end of said channel to cover and protect said needle with said first member upon removal of the external force.

7. A safety device as recited in claim 6 wherein said biasing means is a spring.

8. A system for safely removing the sheath from a sheathed prefilled injection syringe that has an attached elongated needle guard that defines an axis, and for reconfiguring the distal tip of the needle guard to be radially proximate to the syringe needle, said system comprising:
   a ring for reconfiguring the distal tip of the needle guard, said ring being positionable over the needle guard and moveable from a first position, wherein the distal tip of the needle guard is in a radially expanded configuration to allow the sheath to pass through the distal tip during attachment of the needle guard to the syringe, to a second position wherein the distal tip of the needle guard is radially proximate to the syringe needle; and
   a cover positionable over said needle guard and engageable with said ring and the sheath of the syringe, said cover having a means for removing said sheath from said prefilled syringe and for moving said ring from said first position to said second position to reconfigure the distal tip of the needle guard, as said cover is withdrawn from the needle guard.

9. A system as recited in claim 8 wherein said system further comprises a lug that is attached to said ring, said lug extending radially outwardly from said ring.

10. A system as recited in claim 9 wherein said cover is formed as an elongated tube centerable along said axis, said tube being formed with a linear slot aligned substantially parallel to said axis with said lug insertable into said slot, said slot having a proximal end to engage said lug and said ring during movement of said cover relative to the needle guard to move said ring from said first position to said second position.

11. A system as recited in claim 10 wherein said elongated tube is substantially cylindrical in shape.

12. A system as recited in claim 8 wherein said cover is formed as an elongated tube having an open end to allow the cover to be inserted over the needle guard and a partially closed end, said partially closed end formed with an aperture for receiving the sheath of the prefilled injection syringe and affixing the sheath to the cover to allow the sheath to be removed from the prefilled injection syringe when the cover is withdrawn from the needle guard.

13. A system for safely removing the sheath from a sheathed prefilled injection syringe that has an attached needle guard, and reconfiguring the distal tip of the needle guard to be radially proximate to the syringe needle, said system comprising:
   a means for reconfiguring the distal tip of the needle guard from an expanded configuration wherein said distal tip of said needle guard is distanced from the syringe needle to allow the sheath to pass through the needle guard during attachment of the needle guard to the syringe, to a configuration wherein the distal tip of the needle guard is proximate to the syringe needle to cover and protect the syringe needle after an injection; and
   a means for removing said sheath from said prefilled syringe and for activating said reconfiguring means.

14. A system as recited in claim 13 wherein said reconfiguring means comprises a ring, said ring being positionable over the needle guard and moveable from a first position, wherein the distal tip of the needle guard is in said expanded configuration to a second position wherein the distal tip of the needle guard is proximate to the syringe needle.

15. A system as recited in claim 14 wherein said ring defines an axis and said reconfiguring means further comprises a lug that is attached to said ring and extends radially from said ring.

16. A system as recited in claim 15 wherein said removing and activating means comprises a cover for insertion over the needle guard, said cover being formed as an elongated tube centerable along said axis, said tube being formed with a linear slot aligned substantially parallel to said axis with said lug insertable into said slot, said slot having a proximal end to engage said lug and said ring during movement of said cover relative to the needle guard to move said ring from said first position to said second position.

17. A system as recited in claim 13 wherein said removing and activating means comprises a cover formed as an elongated tube having an open end to allow the cover to be inserted over the needle guard and a partially closed end, said partially closed end formed with an aperture for receiving the sheath of the prefilled injection syringe and affixing the sheath to the cover to allow the sheath to be removed from the prefilled injection syringe when the cover is withdrawn from the needle guard.

18. A system as recited in claim 17 wherein said aperture is defined by a surrounding edge, said edge being distally tapered to allow the sheath to pass into said aperture during insertion of said cover on the needle guard and to hold the sheath during withdrawal of said cover from the needle guard.

19. A system as recited in claim 17 wherein said elongated tube is substantially cylindrical in shape.

* * * * *

UNITED STATES PATENT AND TRADEMARK OFFICE
CERTIFICATE OF CORRECTION

PATENT NO. : 6,648,858 B2  Page 1 of 1
DATED : November 18, 2003
INVENTOR(S) : Hooman A. Asbaghi It is certified that error appears in the above-identified patent and that said Letters Patent is hereby corrected as shown below:

<u>Column 8,</u>
Line 12, delete "FIG. 14." insert -- FIGS. 1-4. --

Signed and Sealed this

Sixteenth Day of March, 2004

JON W. DUDAS
*Acting Director of the United States Patent and Trademark Office*